| United States Patent [19] | [11] | 4,102,806 |
|---|---|---|
| Kondo et al. | [45] | Jul. 25, 1978 |

[54] METHOD OF PRODUCING MICROCAPSULES AND RESULTING PRODUCT

[75] Inventors: Sadao Kondo, Kawanishi; Hidehiko Nakano, Suita, both of Japan

[73] Assignee: Takeda Chemical Industries, Ltd., Japan

[21] Appl. No.: 715,192

[22] Filed: Aug. 17, 1976

[30] Foreign Application Priority Data

Aug. 18, 1975 [JP] Japan ................................ 50-100363

[51] Int. Cl.² ............................................ B01J 13/02
[52] U.S. Cl. .................................... 252/316; 71/64 F; 424/19; 424/38; 424/93; 424/94; 424/147; 424/154; 424/181; 424/201; 424/203; 424/227; 424/230; 424/250; 424/251; 424/255; 424/263; 424/279; 424/280; 424/315; 424/319; 424/329; 424/346; 426/72; 426/805
[58] Field of Search ................. 252/316; 424/38, 181, 424/19; 426/805, 72; 195/DIG. 9; 71/64 F

[56] References Cited

U.S. PATENT DOCUMENTS

| 2,805,977 | 9/1957 | Robinson et al. ................. 424/38 X |
| 2,875,130 | 2/1959 | Grass, Jr. et al. ................. 424/38 X |
| 2,967,177 | 1/1961 | Johnson et al. .................. 424/181 X |
| 3,082,154 | 3/1963 | Allan ..................................... 424/38 |
| 3,196,018 | 7/1965 | Galler ..................................... 426/72 |
| 3,415,758 | 12/1968 | Powell et al. ......................... 252/316 |
| 3,541,204 | 11/1970 | Sibbald et al. .......................... 424/38 |
| 3,584,114 | 6/1971 | Cavalli et al. .......................... 424/38 |
| 3,960,757 | 6/1976 | Morishita et al. .................... 252/316 |

*Primary Examiner*—Richard D. Lovering
*Attorney, Agent, or Firm*—Wenderoth, Lind & Ponack

[57] ABSTRACT

A novel and industrially feasible method of producing microcapsules, which comprises dissolving an oil-and-fat in an organic solvent by heating, dispersing a core material in the resultant solution, cooling the dispersion with stirring to coacervate the oil-and-fat on the core material, and separating and drying the resultant encapsulated particulate products.

32 Claims, No Drawings

METHOD OF PRODUCING MICROCAPSULES AND RESULTING PRODUCT

This invention relates to a method comprising encapsulating a particulate core material with an oleaginous material in an organic solvent.

Among the encapsulating methods employing oleaginous materials by way of shell-forming component is the fusing method which comprises heating an oleaginous material until it is fused and coating a core material with the resultant melt in a suitable vehicle, another known method comprising the steps of dissolving an oleaginous material in a solvent, dispersing a particulate core material in the solution, and removing the solvent in a suitable manner so as to leave the individual cores coated with said oleaginous material, the latter method being known as the organic solvent method. The fusing method has two versions, one comprising the use of a gaseous phase as the vehicle and the other employing a liquid phase as the vehicle. While both processes are fully practical for the encapsulation of some core materials, the following disadvantages are unavoidable. Thus, where a gaseous phase is used as the vehicle, large-scale spray-chilling equipment must be provided. In the process employing a liquid phase as the vehicle, particularly where said phase is water, for instance, a water-soluble core material will partially migrate into the vehicle to cause a waste of material or its decomposition may be encouraged by the presence of water. Non-aqueous solvents, which are of necessity limited to certain special high-boiling varieties, cannot be easily removed later.

In the organic solvent method, the separation or evaporation of the solvent is normally carried out in an aqueous phase and, therefore, the method is unsuited for the encapsulation of water-soluble core materials. As a modification of the organic solvent method, there is a process wherein, after dissolution of the encapsulating or shell-forming material in an organic solvent, a non-solvent is added to the solution to depress the solubility in the system until coacervation takes place between the shell-forming material and the solvent, thereby achieving the desired encapsulation. However, the process requires a large quantity of non-solvent and its subsequent recovery presents a major problem.

This invention is characterized in that, while it takes advantage of this phenomenon of coacervation, it does not rely on the use of a non-solvent to accomplish the desired encapsulation but achieves the desired coacervation of the oleaginous component from the solvent by mere temperature adjustment.

Thus, the principal object of the present invention is to provide a novel and industrially feasible method of producing microcapsules. Other objects will be clear from the description and claims hereinafter.

The novel method of the present invention for producing a microencapsulated product, comprises (a) dissolving an oil-and-fat in an organic solvent by heating, said oil-and-fat being solid at room temperature, said organic solvent being hardly or not capable of dissolving a core material to be encapsulated but capable of dissolving said oil-and-fat when hot and capable of coacervating said oil-and-fat when cold, (b) dispersing said core material in the resultant solution, (c) cooling the dispersion with stirring to coacervate the oil-and-fat on the core material, and (d) separating and drying the resultant encapsulated particulate product.

"Oil-and-fat" is mainly composed of glycerin ester of fatty acids (Encyclopedia of Polymer Science and Technology, published by John Wiley & Sons Inc. Vol. 1, 98). The oil-and-fat usable in this invention is solid at room temperature and has a melting point not lower than 30° C, preferably not lower than 50° C, and further preferably not lower than 60° C. The oil-and-fat is exemplified by hydrogenated oil-and-fat (e.g. hydrogenated castor oil, hydrogenated soybean oil, hydrogenated rapeseed oil, hydrogenated beef tallow, hydrogenated palm oil, hydrogenated cottonseed oil, hydrogenated fish oil, hydrogenated whale oil), solid fat (e.g. cacao butter, lard, beef tallow), synthetic solid glyceride (e.g. glycerin monostearate, glycerin distearate, glycerin tristearate) and so on. Among them, hydrogenated oil-and-fat and cacao butter are advantageous, and especially advantageous is hydrogenated oil-and-fat having a melting point not lower than 50° C, preferably not lower than 60° C such as hydrogenated, castor oil, hydrogenated soybean oil and so on. These materials may be employed alone or as mixture and in the latter case they may be partially replaced by those oils-and-fats which are liquid at room temperature.

The organic solvent may be any appropriate organic solvent, provided that, when hot, it is able to dissolve said oil-and-fat, that the core material to be encapsulated is hardly soluble or insoluble therein and that, when cold, the solvent will coacervate the oil-and-fat to allow the latter to encapsulate the core material. Preferred are the solvents which, when hot, will dissolve not less than 1 percent (weight/volume), desirably not less than 5 percent, of said oil-and-fat and, when cold, will coacervate not less than 50 percent of the dissolved oil-and fat.

Examples of said organic solvents are lower alkanol of up to six carbon atoms (e.g. methanol, ethanol, n-propanol, iso-propanol, n-butanol, iso-butanol, n-amyl alcohol, iso-amy alcohol), saturated hydrocarbon (e.g. n-hexane, cyclohexane), ethyl ether, ethylene glycol monomethyl ether, ethyl acetate, acetone, benzene, trichloroethylene and so on. Among them, advantageous are the lower alkanol and the saturated hydrocarbon, especially methanol, ethanol, n-propanol, iso-propanol, n-hexane and cyclohexane. These solvents may be employed alone or as mixture. In mixture, advantageous is a mixture of lower alkanol and saturated hydrocarbon.

Table 1 shows some examples of the preferred combinations of oils-and-fats with solvents.

Table 1

| Combinations of oils-and-fats with solvents | |
|---|---|
| Oil-and-fat | Solvent |
| Hydrogenated castor oil | Methanol |
| | Ethanol |
| | n-Propanol |
| | iso-Propanol |
| | n-Amyl alcohol |
| | Ethylene glycol monomethyl ether |
| | Ethyl acetate |
| | Acetone |
| | Benzene |
| | n-Hexane |
| | Trichloroethylene |
| | Ether |
| Hydrogenated beef tallow | Ethanol |
| Cacao butter | Ethanol |
| Glycerin monostearate | Ethanol |
| Mixture of hydrogenated castor oil and hydrogenated soybean oil | Ethanol |

The particulate core material may be whichever of a water-soluble and a water-insoluble material, all that is necessary being that it is solid at room temperature and is either hardly soluble or insoluble in said vehicle. Said core material may have a diameter within the range of 0.1 micron to several millimeters (e.g. 3 millimeters) and, preferably, between 10 microns and 840 microns. These core materials may be any of feed additives, medicines, agricultural chemicals, food additives and so on.

Examples of said core materials are vitamins, minerals, amino acids, antibiotics, synthetic antibacterial or antiprotazoal agents, analgesic antipyretics, enzymes, dried viable microorganisms, feed or food materials, agricultural chemicals and so on. Among them, advantageous are vitamins, antibiotics and enzymes.

Said vitamins are exemplified by thiamine salts and their derivatives (e.g. thiamine mononitrate, thiamine hydrochloride, thiamine tetrahydrofurfuryl disulfide and its hydrochloride, thiamine propyl disulfide and its hydrochloride), pyridoxine hydrochloride, hydroxocobalamine, cyanocobalamine, menadione and its derivatives (e.g. menadione sodium bisulfite, menadione sodium bisulfite complex, menadione dimethylpyrimidinol bisulfite), acetomenaphtone, folic acid, ascorbic acid and its salts (e.g. ascorbic acid, sodium ascorbate, calcium ascorbate), choline chloride, nicotinic acid, nicotinamide and so on.

The minerals are exemplified by potassium iodide, calcium iodate, ferrous sulfate, ferrous fumarate, ferrous threonate and so on.

The amino acids are exemplified by methionine, lysine hydrochloride and so on.

The antibiotics are exemplified by macrolide antibiotics (e.g. oleandomycin, oleandomycin phosphate, triacetyl oleandomycin, kitasamycin, kitasamycin tartrate, kitasamycin succinate, kitasamycin stearate, acetyl kitasamycin, erythromycin, erythromycin ethyl succinate, erythromycin ethyl carbonate, erythromycin stearate, erythromycin propionate, erythromycin propionate lauryl sulfate, T2636 disclosed in Journal of Antibiotics, Vol. 24, No. 1, page 1-12, 1970), tetracyclines (e.g. tetracycline, tetracycline hydrochloride, tetracycline metaphosphate, oxytetracycline, oxytetracycline hydrochloride, ammonium oxytetracyclinate, metacycline hydrochloride, demethyl chlortetracycline, chortetracycline, calcium chlortetracyclinate, chlortetracycline hydrochloride, pyrrolidinomethyltetracycline, tetracycline methylene lysine), penicillins (e.g. sodium penicillin, potassium penicillin, aluminum penicillin, calcium penicillin, benzyl penicillin, benzyl penicillin benzathine, procaine benzyl penicillin, sodium benzyl penicillin, potassium benzyl penicillin, benzyl penicillin aminomethomidine, ampicillin, sodium oxacillin, sodium dicloxacillin, potassium propicillin, phenoxymethyl penicillin benzathine, sodium phenoxymethyl penicillin, calcium phenoxymethyl penicillin, potassium phenoxymethyl penicillin, potassium phenethicillin), cephalosporins (e.g. cephalexin, cephaloglycin), polypeptide antibiotics (e.g. bacitracin, zinc bacitracin, manganese bacitracin, colistin, colistin sulfate, colistin hydrochloride, colistin sodium methanesulfonate, enramycin (enduracidin) hydrochloride, thiopeptin), aminoglycosidic antibiotics (e.g. kanamycin sulfate, fradiomycin sulfate, tobramycin, gentamycin), polyether antibiotics (e.g. T-42082 disclosed in Japanese Patent Publication No. 35494/1976) and other antibiotics (e.g. spiramycin, acetyl spiramycin, spiramycin embonate, chloramphenicol, chloramphenicol parmitinate, chloramphenicol stearoylglycorate, chloramphenicol succinate, chromomycin $A_3$).

The synthetic antibacterial or antiprotozoal agents are exemplified by amprolium, beclotiamine naphthalene-1,5-disulfonate, ethyldimethialium nitrate, dimethialium nitrate, 3-sulfanilamidoisoxazole, 3-sulfanilamidoisoxazole sodium, sulfamethazine, sulfamethazine sodium, sulfamonomethoxine, sulfamonomethoxine sodium, sulfadimethoxine, sulfadimethoxine sodium, sulfaquinoxaline, sulfaquionoxaline sodium, pyrimethamine and so on.

The analgesic antipyretics are exemplified by aspirin, aluminum aspirin and so on.

The enzymes are exemplified by phycomyces lipase, serratia peptidase, aspergillo peptidase, trypsin, diastase, cellulase and so on.

The dried viable microorganisms are exemplified by Streptococcus faecalis, Lactobacillus acidophilus, Lactobacillus salivarus, Lactobacillus bifidus and so on.

The feed or food materials are exemplified by 5'-ribonucleotide, sodium bicarbonate, citric acid, tartaric acid, succinic acid, dried yeast extract and so on.

The agricultural chemicals include pesticides, herbicides, fertilizers or the like, and are exemplified by chlorophenamidine hydrochloride, cartap hydrochloride and so on.

These core materials may be employed alone or as mixture, or may be employed together with a suitable carrier or stabilizer, for example, ascorbic acid-corn starch, menadion dimethylpyrimidinol bisulfite-calcium dihydrogenphosphate and so on.

The dissolution of the oil-and-fat is effected by increasing the temperature of the organic solvent but not to a level as high as to decompose the core material. An advantageous range of the temperature is 50° C to 100° C. In order to dissolve as much of this shell-forming component as possible, it is recommended that the solvent would be heated to a temperature near its boiling point. The dissolution may be carried out with refluxing the solvent so that the system may be stirred spontaneously. The resultant solution has generally a viscosity lower than 100 centipoises, advantageously lower than 50 centipoises.

The dispersion of the core material to the solution is effected at a temperature higher than the temperature at which the coacervation appears. An advantageous range of the temperature is 30° C to 100° C, and when the core material which is changeable at a high temperature, for example, enzyme or dried viable microorganism, is employed, advantageous is a temperature not higher than 40° C.

The stirring to be performed at the dispersion step of the core material into the shell-forming material and at the cooling step need not be especially vigorous but, rather, gentle stirring of the order barely enough to preclude a sedimentation or caking of the core material is sufficient. By increasing the stirring speed, the resultant encapsulated products may be obtained in a smaller size. The particle size of the products may be also dependent upon other factors such as the core material, oil-and-fat, etc.

The resultant dispersion is cooled to a temperature within the range from 0° C to 60° C, advantageously from 20° C to 45° C. As to the cooling operation, the system may be allowed to cool under room temperature conditions but, to reduce the encapsulation time, forced cooling with water or other cooling medium may also be employed. However, because excessively rapid cooling would cause the shell-forming material to be coacervated in isolation from the core material, it is desirable to reduce the temperature gradually once the system has approached the temperature at which the shell-forming material would start coacervating from the solvent. Generally, the coacervation of an oil-and-fat takes place at a temperature far below the temperature at which it was dissolved. By way of example, hydrogenated castor oil as dissolved in ethanol at 78° C would start undergoing coacervation in the neighborhood of 50° C and, as it has been discovered, this coacervation continues for a fairly long time even after the temperature of the system has dropped to room temperature, i.e. 25° to 30° C. Therefore, in order that the oil-and-fat dissolved in a solvent may be allowed to coacervate sufficiently from the solvent, it is necessary that the solution be maintained, under stirring, at the destination temperature of cooling for some time. While the appropriate duration of this time depends upon such variables as the shell-forming material, organic solvent, destination temperature, batch size, etc., it is generally within the range of 10 minutes to 2 hours, advantageously 30 minutes to 2 hours. Where an oil-and-fat melting at 50° C or less or having high solubility to the solvent is employed as the shell-forming material, no satisfactory coacervation may be obtained at times unless the destination temperature of cooling is held below room temperature. Taking cacao butter as an example, it has been found that the butter separates out from the solvent ethanol when the solution is cooled to a temperature not higher than 5° C.

The encapsulated product can then be separated from the vehicle by a known procedure, exemplified by filtration, centrifugation, adsorption on a suitable particulate solid and so on. From the resultant wet particulate product, the solvent is removed by a procedure known per se at a temperature below the fusing point of the employed oil-and-fat, for example by drying under reduced pressure, in hot air currents or in a fluidized bed or by the spray-drying method, whereby the product can be recovered as independent, free-flowing microcapsules.

In this invention, the ratio of organic solvent to core material is at least 3:1 V/W (not less than 3 ml per gram), advantageously at least 5:1 V/W (not less than 5 ml per gram) and a greater amount of the solvent is necessary where the solubility of the oil-and-fat in the solvent is low. Furthermore, the ratio of the oil-and-fat, which is the shell-forming component, to the core material in the solvent may be optional within the limits of 0.1:1 to 10:1, preferably within the limits of 0.3:1 to 5:1, further preferably wthin the limits of 0.75:1 to 2:1.

In this invention, a polymer may be dissolved in the organic solvent together with the fat-and-oil. The polymer takes a part to support oleocapsule in the encapsulated product under high temperature, for example, a temperature when feed pellet is formed, or a part to make the microcapsule possess a suitable property for sustained release or prolonged action. The polymer is generally dissolved in the organic solvent at a concentration not greater than 5 W/V percent, advantageously at a concentration not greater than 2 W/V percent. In this case, the viscosity of the resultant solution is lower than 100 centipoises, preferably lower than 50 centipoises in the presence of the oil-and-fat. In the above concentration, the polymer itself does not coacervate or precipitate in the system, and, therefore, the polymer in encapsulated product is based upon that dissolved in the solvent which was contained in gel structure of the coacervated oleocapsule. Accordingly, the ratio of the polymer to the oil-and-fat in the resultant oleocapsule is generally not greater than 25 percent by weight basis, advantageously not greater than 10 percent by weight basis. Said polymers are exemplified by cellulose derivatives (e.g. hydroxypropyl cellulose, hydroxypropylmethyl cellulose, cellulose acetate N,N'-di-n-butylhydroxypropylether, cellulose acetate phthalate, ethyl cellulose, methyl cellulose), acrylic copolymers (e.g. dimethylaminoethyl methacrylate-methyl methacrylate copolymer, 2-methyl-5-vinylpyridine-methyl acrylatemethacrylic acid copolymer, methacrylate-methacrylic acid copolymer, methyl methacrylate-methacrylic acid copolymer), polyvinylacetal diethylaminoacetate and so on. These materials may be employed alone or as mixture.

In a case that the polymer is employed in this invention, if necessary, a fine powder [e.g. corn starch, lactose, magnesium, stearate, stearate, talc, silicic acid anhydride, SIPERNANT 17 (made by Degussa Co., West Germany)] may be added to the solution after coacervation in order to prevent the adherence among the resultant encapsulated products.

In step (d) of this invention, the resultant dried particulate product may be further mixed with a powdery hydrophobic carrier (e.g. magnesium stearate, aluminum stearate, talc, SIPERNANT 17), heated and then cooled. The heating is carried out at a temperature higher than a melting point of the employed oil-and-fat by degrees not more ten in centigrade. Said temperature is generally from 30° C to 90° C and maintained for 10 minutes to 30 minutes. The amount of the powdery hydrophobic carrier, which is employed in order to prevent the adherence among the microencapsulated products at heating, may be generally 0.1 to 5 times of the microencapsulated product by weight basis. The cooling is carried out to a temperature lower than a melting point of the employed oil-and-fat. By this heating and cooling, the density of the oleocapsule is heightened and thereby the oleocapsule wall is strengthened. In this procedure, the oleocapsule which contains the polymer with the oil-and-fat is advantageously employed.

The method according to this invention does not require a non-solvent (a solvent which is otherwise employed to depress the solubility of shell-forming material in a system to cause a coacervation) and requires only a comparatively small amount of a solvent. Moreover, low-boiling alcohols, saturated hydrocarbons and other solvents that are easy to remove later can be successfully employed. Since non-aqueous solvents may also be employed, the method of this invention has the advantage that those kinds of core materials which are readily soluble in water or unstable in the presence of water can also be encapsulated without causing a loss of the ingredients. Moreover, since the coacervation of this invention is caused by only temperature adjustment, this method is very advantageous in industrial applications.

The encapsulated product obtained in the above manner may as such be employed in various applications, e.g. as feed additives, medicines, agricultural chemicals, food additives and so forth, and is excellent in stability of the core material. The encapsulated product may also be diluted with other suitable particulate materials to manufacture powders or processed into tablets or granules together with other suitable compounding ingredients according to appropriate formulas or prescriptions. The microencapsulated product obtained by the foregoing method of this invention may also be used further as a core material for encapsulation by a known method.

The following examples are further illustrative but by no means limitative of this invention.

EXAMPLE 1

To 80 ml of ethanol was added 5.0 g of Castor Wax A (Nihon Yushi Ltd., Japan hydrogenated castor oil, melting point 85° C) and, in a flask fitted with a reflux condenser, the mixture was boiled at 78° C. The resultant solution was transferred to a beaker of stainless steel, to which 5.0 g. of calcium ascorbate (80-200 mesh; Takeda Chemical Industries, Ltd., Japan) was added. Under agitation with a propeller stirrer, the mixture was allowed to cool under room temperature conditions whereby Castor Wax A was caused to coacervate on the calcium ascorbate by way of core material and, thereby, to produce an encapsulated particulate product. This system was centrifuged to remove the ethanol and dried under reduced pressure and at 40° C for 3 hours. By the above procedure was obtained 9.0 g of calcium ascorbate oleocapsules from 48 to 200 mesh in diameter.

EXAMPLE 2

To 1.0 g of Castor Wax A was added 80 ml of n-hexane and, in a flask fitted with a reflux condenser, the mixture was boiled at 69° C. The resultant solution was transferred to a beaker of stainless steel, in which 1.0 g of calcium ascorbate from 80-200 mesh was added. Thereafter, the corresponding procedure of Example 1 was repeated to obtain 1.5 g of calcium ascorbate oleocapsules from 48 to 200 mesh in diameter.

EXAMPLE 3

To 1.0 g of hydrogenated beef tallow (Nihon Yushi Ltd., Japan, melting point 45° C) was added 50 ml of ethanol and, with a reflux condenser, the mixture was boiled at 78° C. The resultant solution was transferred to a beaker of stainless steel, in which 1.0 g of calcium ascorbate from 48-200 mesh was added. Thereafter, the corresponding procedure of Example 1 was repeated to obtain 1.3 g of oleocapsules of calcium ascorbate from 48-200 mesh in diameter. The cooling temperature used, however, was 0° C in ice-water.

EXAMPLE 4

To 2.0 g of cacao butter (Fuji Seiyu Ltd., Japan, melting point 30°-35° C) was added 80 ml of ethanol and, in a flask fitted with a reflux condenser, the mixture was boiled at 78° C. The resultant solution was transferred to a beaker of stainless steel, in which 2.0 g of calcium ascorbate from 80-200 mesh was added. Under stirring with a propeller stirrer, the mixture was cooled to 0° C, whereby the cacao butter was coacervated on the calcium ascorbate cores to yield an encapsulated product. The system was centrifuged to remove the ethanol and the solid was dried under reduced pressure and at 25° C for 8 hours. By the above procedure was obtained 3.8 g of calcium ascorbate oleocapsules with diameters in the range of 48 to 200 mesh.

EXAMPLE 5

To 2.0 g of glycerin monostearate (Riken Vitamin Oil Ltd., Japan, melting point 58.5°-62.0° C) was added 80 ml of ethanol and, with a reflux condenser, the mixture was boiled at 78° C. The resultant solution was transferred to a beaker of stainless steel, in which 2.0 g of calcium ascorbate from 80-200 mesh was added. Thereafter, the corresponding procedure of Example 1 was repeated to obtain 3.9 g of calcium ascorbate oleocapsules from 48 to 200 mesh in diameter.

EXAMPLE 6

5.0 g of Castor Wax A and 5.0 g of soybean oil (The Pharmacopoeia of Japan were taken and 80 ml of ethanol was added. After a reflux condenser was attached, the mixture was boiled at 78° C. The resultant solution was transferred to a beaker of stainless steel, in which 5.0 g of calcium ascorbate from 80 to 200 mesh was added. Thereafter, the corresponding procedure of Example 1 was repeated to obtain 13.4 g of calcium ascorbate oleocapsules from 48 to 200 mesh in diameter.

EXAMPLE 7

The procedure of Example 1 was repeated except that 5.0 g of dry iron sulfate not exceeding 200 mesh (The Pharmacopoeia of Japan) was used in lieu of calcium ascorbate. By this procedure was obtained 8.8 g of oleocapsules of dry iron sulfate from 32 to 100 mesh in diameter.

EXAMPLE 8

The procedure of Example 1 was repeated except that 1.0 g of aluminum aspirin (average diam. about 5 $\mu$) was used in lieu of calcium ascorbate to obtain 4.7 g of aluminum aspirin oleocapsules from 60 to 100 mesh in diameter.

EXAMPLE 9

To 2.0 g of Castor Wax A was added a mixture of 40 ml ethanol and 40 ml n-hexane and, with a reflux condenser, the system was heated at 70° C. The resultant solution was transferred to a beaker of stainless steel, in which 2.0 g of calcium ascorbate, 80 to 200 mesh, was added. Thereafter, the corresponding procedure of Example 1 was repeated to obtain 3.8 g of calcium ascorbate oleocapsules from 48 to 200 mesh in diameter.

EXAMPLES 10-51

(1) Producing Procedure

A. To a solid oil-and-fat was added a solvent or a mixture of solvents and, with a reflux condenser, the system was heated at a temperature near the boiling point of the solvent. The resultant solution was transferred to a beaker of stainless steel, to which a core material was added. Under agitation with a propeller stirrer, the mixture was allowed to cool under room temperature conditions, if necessary with making use of ice, whereby the oil-and-fat was coacervated around the core material and, thereby, to produce an encapsulated particulate product. This system was filtrated or centrifuged to remove the solvent and dried under reduced pressure and at room temperature for 16 hours.

B. To a solid oil-and-fat and polymer was added a solvent or a mixture of solvents and, with a reflux condenser, and processed in the same manner as in Procedure A. After coacervation, if necessary fine powders such as Corn starch, Lactose, etc. were added to the solvent to prevent the microcapsules from the adhesion of particles.

(2) Results

The formulation, producing condition, and the yield and particle size of the resultant microcapsules are shown in Table 2.

Table 2

| Example No. | Core material | solid oil-and-fat | Polymer | Solvent | Temperature of dispersing core material | Microcapsule Yield | Particle size | Procedure | Fine powder dispersed in solvent |
|---|---|---|---|---|---|---|---|---|---|
| 10 | Sodium ascorbate(100-200 mesh;Takeda Chemical Industries, Ltd.,Japan) ; 1 g | Castor Wax A(Nihon Yushi Ltd., Japan, hydrogenated castor oil, m.p. 85° C); 2g | None | n-hexane ;80ml n-propanol ;5ml | 53° C | 1.29g | 16-100$^{mesh}$ | A | None |
| 11 | "; 5g | "; 10g | None | n-hexane ;400ml iso-propanol ;25ml | 60°C | 9.38g | 16-80$^{mesh}$ | A | None |
| 12 | "; 5g | "; 10g | Ethocel STD$^{3)}$ ;3.5g | " | 52° C | 10.17g | 16-120$^{mesh}$ | B | None |
| 13 | "; 1g | L.B.Wax$^{1)}$ (Nihon Yushi Ltd., Japan m.p. 60° C) ;2g | None | ethanol; 80ml | 61° C | 1.52g | 16-100$^{mesh}$ | A | None |
| 14 | "; 1g | Lubri Wax 102$^{2)}$ (Freund Ind. Co.,Ltd. Japan,m.p. 62° C);2g | None | n-hexane ;80ml | 52° C | 2.38g | 32-100$^{mesh}$ | A | None |
| 15 | "; 50g | hydrogenated beef tallow (Nihon Yushi Ltd. Japan, m.p.60° C); 100g | None | ethanol ;1200ml | 65° C | 117.5g | 32-100$^{mesh}$ | A | None |
| 16 | "; 50g | Castor Wax A;50g | None | n-hexane ;1200ml trichloroethylene ;50ml | 70° C | 82.1g | 16-100$^{mesh}$ | A | None |
| 17 | "; 50g | "; 100g | None | " | 70° C | 125.1g | 16-100$^{mesh}$ | A | None |
| 18 | "; 10g | "; 20g | Ethocel STD ;3g | n-hexane ;800ml n-propanol ;50ml | 60° C | 22.5g | 32-100$^{mesh}$ | B | corn starch ;5g |
| 19 | ascorbic acid (100-200mesh; Takeda Chemical Industries Ltd.,Japan) ;1g | "; 2g | HPC-L$^{4)}$ ;0.7g | n-hexane ;80 ml n-propanol ;5 ml ethanol ;10ml | 60° C | 1.8g | 16-60$^{mesh}$ | B | None |
| 20 | menadione dimethyl-pyrimidinol bisulfite ( 100-200mesh) ;1g | Castor Wax A ;2g | None | n-hexane ;80ml trichloroethylene ;5ml | 52° C | 2.0g | 32-100$^{mesh}$ | A | None |
| 21 | "; 1g | "; 2g | Ethocel STD ;0.7g | n-hexane ;80ml trichloroethylene ;5ml | 54° C | 2.0g | " | B | None |
| 22 | menadione dimethyl-pyrimidinol bisulfite( 100-200mesh) ;1g | Castor Wax A ;2g | Ethocel STD ;0.7g | n-propanol ;5ml n-hexane ;80ml trichloroethylene ;5ml | 53° C | 1.8g | 32-100$^{mesh}$ | B | None |
| 23 | "; 1g | Lubri Wax 102;2g | None | iso-propanol ;5ml n-hexane ;80ml | 52° C | 2.2g | " | A | None |
| 24 | "; 1g | "; 2g | CAP$^{5)}$ ;0.7g | acetone ;80ml | 52° C | 2.1g | 32-100$^{mesh}$ | B | None |
| 25 | "; 1g | L.B.Wax;2g | None | ethanol ;80ml | 61° C | 1.3g | 16-200$^{mesh}$ | A | None |

Table 2-continued

| Example No. | Core material | solid oil- and-fat | Polymer | Solvent | Temperature of dispersing core material | Microcapsule Yield | Microcapsule Particle size | Procedure | Fine powder dispersed in solvent |
|---|---|---|---|---|---|---|---|---|---|
| 26 | menadione sodium bisulfite (200-300mesh);1g | Castor Wax A;2g | None | n-hexane;80ml n-propanol;5ml | 52° C | 1.7g | 16-100$^{mesh}$ | A | None |
| 27 | ";1g | L.B.Wax;2g | None | iso-propanol;80ml | 66° C | 1.3g | 32-200$^{mesh}$ | A | None |
| 28 | menadione dimethyl-pyrinidinol bisulfite (100-200 mesh);1g | Castor Wax A;2g | None | n-hexane;80ml n-propanol;5ml | 53° C | 1.5g | 32-100$^{mesh}$ | A | None |
| 29 | folic acid (100-200mesh);1g | Castor Wax A;2g | None | n-hexane;80ml n-propanol;5ml | 53° C | 2.2g | 16-60$^{mesh}$ | A | None |
| 30 | ";1g | ";2g | Ethocel STD;0.7g | n-hexane;80ml ethanol;10ml | 52° C | 3.1g | " | B | Lactose;1g |
| 31 | ";1g | Lubri Wax 102;2g | None | n-hexane;80ml iso-propanol;5ml | 52° C | 1.8g | " | A | None |
| 32 | ";0.2g | hydrogenated beef tallow;2g | None | n-hexane;80ml | 52° C | 1.3g | 32-200$^{mesh}$ | A | None |
| 33 | folic acid (100-200mesh) 0.2g | L.B.Wax;2g | None | n-hexane;80ml | 53° C | 1.2g | 32-200$^{mesh}$ | A | None |
| 34 | thiamine mononitrate (200-300mesh);1g | Castor Wax A;2g | None | n-hexane;80ml iso-propanol;5ml | 52° C | 1.3g | 16-200$^{mesh}$ | A | None |
| 35 | thiamine tetrahydro-furfuryl disulfide (60-200mesh);1g | Castor Wax A;2g | None | " | " | 1.2g | 16-60$^{mesh}$ | A | None |
| 36 | pyridoxine hydrochloride (60-200mesh);1g | " | None | " | " | 1.4g | " | A | None |
| 37 | cyano-cobalamin (200-300mesh);1g | " | None | " | " | 1.1g | " | A | None |
| 38 | choline chloride (16-32mesh);1g | Castor Wax A;2g | | n-hexane;80ml iso-propanol;5ml | 53° C | 0.8g | 9-32$^{mesh}$ | A | None |
| 39 | DL-methionine (60-200mesh);1g | " | None | " | 51° C | 1.6g | 16-60$^{mesh}$ | A | None |
| 40 | L-lysine hydrochloride (60-200mesh);1g | " | None | " | 53° C | 1.3g | 16-80$^{mesh}$ | A | None |
| 41 | calcium iodate(100-300mesh);1g | " | None | " | 52° C | 1.0g | 16-60$^{mesh}$ | A | None |
| 42 | 5'-ribo-nucleotide (60-200mesh);1g | " | None | " | 51° C | 0.8g | 16-100$^{mesh}$ | A | None |
| 43 | Chloro-phenamidine hydro-chloride(32-100mesh);1g | Castor Wax A;2g | None | n-hexane;80ml iso-propanol;5ml | 52°C | 1.4g | 16-60$^{mesh}$ | A | None |
| 44 | Cartap hydro-chloride(200-300 mesh);1g | None 2g | " | 52° C | 1.1g | " | A | None | |
| 45 | T-2636$^{6)}$;1g | ";2g | None | n-hexane;80ml n-propanol;5ml | 52° C | 1.6g | 16-60$^{mesh}$ | A | None |
| | triacetyl- | | | n-hexane | | | | | |

Table 2-continued

| Example No. | Core material | solid oil-and-fat | Polymer | Solvent | Temperature of dispersing core material | Microcapsule Yield | Particle size | Procedure | Fine powder dispersed in solvent |
|---|---|---|---|---|---|---|---|---|---|
| 46 | oleandomycin (60–200mesh) ;1g | "; 2g | None | ;80ml iso-propanol ;5ml | 52° C | 1.2g | " | A | None |
| 47 | tetracycline (200–300mesh) ;1g | Lubri Wax 102;2g | None | n-hexane ;80ml | 52° C | 1.3g | " | A | None |
| 48 | chlortetra-cycline hydrochloride (200–300mesh) ;1g | Castor Wax A;2g | None | n-hexane ;80ml n-propanol ;5ml | 52° C | 1.6g | 16–60$^{mesh}$ | A | None |
| 49 | ethyl-dimethialium nitrate(200-300 mesh; Takeda Chemical Ind.Ltd.);1g | Castor Wax A;2g | None | n-hexane ;80ml iso-propanol ;5ml | 52° C | 1.0g | 32–200$^{mesh}$ | A | None |
| 50 | Phycomyces Lipase(200-300mesh, Takeda Chemical Ind. Ltd.,Japan) ;1g | Castor Wax A;2g | None | n-hexane ;80ml | 52° C | 2.3g | 32–100$^{mesh}$ | A | None |
| 51 | "; 1g | L.B.Wax;2g | None | n-hexane ;80ml | 35° C | 2.3g | 60–120$^{mesh}$ | A | None |

1. hydrogenated castor oil plus hydrogenated soybean oil
2. hydrogenated soybean oil
3. ethyl cellulose (Dow Chem. Co. U.S.A.)
4. hydroxy propyl cellulose (Nihon Soda Ltd., Japan)
5. cellulose acetate phthalate
6. Journal of Antibiotics, Vol. 24, No. 1, page 1-12, 1970

EXAMPLE 52

To 0.4 g of the sodium ascorbate oleocapsules obtained according to Example 12 was added 1.2 g of magnesium stearate as a carrier and mixed well. The mixture was heated at 90° C for 30 minutes and allowed to cool under room temperature conditions, and 50 ml of water and 0.5 ml of 1% starch solution were added. Under agitation with a magnetic stirrer, 0.1N-iodine reagent was added dropwise to determine the percent dissolution of sodium ascorbate into water by plotting the cumulative consumption of iodine on a time axis. The sodium ascorbate oleocapsules obtained according to Example 12 were run as reference control. The results are set forth in Table 3, which shows that the oleocapsules are strengthened by the above treatment, and thereby the dissolution of sodium ascorbate is significantly retarded.

Table 3

| Percent dissolution of sodium ascorbate into water | | | |
|---|---|---|---|
| Test material | Time (min.) | | |
| | 5 | 10 | 20 |
| Sodium ascorlate oleocapsules (Example 12) control | 45 | 70 | 88 |
| Sodium ascorbate oleocapsules (Example 52) | 9 | 16 | 26 |

Test 1

About 400 mg of the calcium ascorbate oleocapsules obtained according to Example 1 were accurately weighed and 50 ml of water and 0.5 ml of 1% starch solution were added. Under agitation with a magnetic stirrer, 0.1N-iodine reagent was added dropwise to determine the percent dissolution of calcium ascorbate into water by plotting the cumulative consumption of iodine on a time axis. Calcium ascorbate in the sizes of 80 to 200 mesh was run as reference control. The results are set forth in Table 4, which shows that the encapsulation significantly retards the dissolution of calcium ascorbate.

Table 4

| Percent dissolution of calcium ascorbate into water | | | | | | | | |
|---|---|---|---|---|---|---|---|---|
| Test material | Time (min.) | | | | | | | |
| | 1 | 2 | 10 | 20 | 30 | 40 | 50 | 60 |
| Calcium ascorbate 80–200 mesh (control) | 99.9 | 100.0 | 100.0 | — | — | — | — | — |
| Calcium ascorbate oleocap-sules, 48–200 mesh | 0.6 | 1.3 | 9.2 | 19.4 | 27.7 | 35.6 | 43.0 | 51.3 |

Test 2

To "Premix for fish feed" shown in Table 5 was added sodium ascorbate oleocapsule of Example 17 or sodium ascorbate as a control so as to make its concentration 5% and, enclosed in a bag of polyethylene and stored under the room temperature conditions in summer in Japan for 12, 21, and 31 days and tested on their stabilities. They were assayed by indophenol colorimetric method.

The results were shown in Table 6.

Table 5

| Formulation of Premix for fish feed (per kg) | |
|---|---|
| Retinol | 667000I.U. |
| Cholecalciferol | 167000I.U. |
| α-tocopherol | 26700I.U. |
| Menadione | 0.667 g |
| Thiamine Mononitrate | 5.0 g |
| Riboflavine | 10.0 g |
| Pyridoxine hydrochloride | 4.0 g |
| Nicotinamide | 26.7 g |

Table 5-continued

| Formulation of Premix for fish feed (per kg) | | |
|---|---|---|
| Calcium pantothenate | 20.0 | g |
| Choline chloride | 200.0 | g |
| Folic acid | 1.34 | g |
| Cyanocobalamine | 3.34 | mg |
| Inositol | 23.4 | g |
| Biotin | 0.0667 | g |
| Manganese sulfate | 10.0 | g (as Mn) |
| Iron fumarate | 16.7 | g (as Fe) |
| Cupric sulfate | 3.34 | g (as Cu) |
| Zinc sulfate | 10.0 | g (as Zn) |
| Calcium iodate | 0.167 | g (as $I_2$) |
| Solvent extracted rice bran | q.s. | |

Table 6

| Stability of sodium ascorbate in Premix | | | | |
|---|---|---|---|---|
| | Initial | 12 days | 21 days | 31 days |
| Sodium ascorbate oleocapsule (Example 17) | mg/g 50.7 (100) | 48.7 (96) | 48.7 (96) | 48.2 (95) |
| Sodium ascorbate (200 Mesh pass) | mg/g 48.2 (100) | 1.0 (2) | 0.5 (1) | 0.3 (1) |

( ): residual percent

Test 3

To the broiler premix shown in Table 7 was added menadion dimethylpyrimidinol bisulfite (MPB) oleocapsules of Example 20 or 21, or MPB as a control so as to make its concentration 1.00 mg/g and, stored in a glass bottle at 40° C for 2 weeks.

They were assayed by gas chromatographic method described in Journal of Association of Official Analytical Chemists, Vol. 56, 1277–1280 W-victor et al. The results were shown in Table 8.

Table 7

| Formulation of broiler premix | |
|---|---|
| Ingredients | Amounts (per Kg) |
| Rovimix AD₃ 500/100** | V.A.*; 3000000I.U. |
| | V.D₃*; 600000I.U. |
| Rovimix E-50** | V.E.*; 3.0 g |
| Thiamine mononitrate | 0.2 g |
| Riboflavine | 3.0 g |
| Pyridoxine hydrochloride | 1.0 g |
| Cyanocobalamine | 0.0025 g |
| Calcium panthothenate | 2.0 g |
| Nicotinamide | 5.0 g |
| Choline chloride | 120.0 g |
| Folic acid | 0.1 g |
| Ferrous sulfate | Fe; 30.0 g |
| Cupric sulfate | Cu; 3.8 g |
| Manganese sulfate | Mn; 25.0 g |
| Zinc sulfate | Zn; 25.0 g |
| Cobaltous sulfate | Co; 0.024 g |
| Solvent extracted rice bran | added to make 1000 g |

*V.A retinol
V.D.₃cholecalciferol
V.E.α-tocopherol
**produced by Hoffman La Roche Co.

Table 8

| Stability of MPB in broiler premix | | |
|---|---|---|
| | Initial | 40° C, 2 weeks |
| MPB oleocapsules; Example 20 | 1.02 mg/g | 1.03 mg/g (101%) |
| MPB oleocapsules; example 21 | 1.01 mg/g | 0.99 mg/g (98%) |
| MPB (100–200 mesh) | 0.92 mg/g | 0.54 mg/g (59%) |

( ) residual percent

Test 4

Phycomyces Lipase oleocapsules of Examples 50 and 51 were tested on their enzymatic stabilities in the process of the encapsulation. Lipase activity was assayed by the method described in Journal of The Takeda Research Laboratries, Vol. 35, 1–10, Tomoda et al.

The reaction mixture containing 5 ml of 25% olive oil emulsified with poly-vinyl alcohol, 4 ml of 0.1M phosphate buffer, pH 7.0 and 1 ml of enzyme solution*, was incubated at 37° C for 50 min. in the Monod shaker. Enzyme reaction was terminated with the addition of 20 ml of acetone : ethanol mixture (1:1 V/V). An amount of liberated fatty acid was titrated with 0.05N NaOH with phenolphthalein as an indicator. One unit of lipase activity was defined as the amount which liberated 1μ mole of free fatty acid per min. at the conditions mentioned above.

* To 100 mg of Phycomyces Lipase oleocapsules or 50 mg of Phycomyces Lipase was added the mixture of 50 ml 0.02 M phosphate buffer and 10 ml trichloroethylene and, shook for 5 min. The upper layer was filtrated with a filter paper (No. 5A)

The results were shown in Table 9. The loss of enzyme activity in the process of the encapsulation was less than 10%.

Table 9

| Stability of Phycomyces Lipase oleocapsules in the process of their productions | | |
|---|---|---|
| Sample | Lipase activity (U/mg) | Specific activity** |
| Phycomyces Lipase | 140 | 66 (100) |
| Phycomyces Lipase oleocapsules; Example 50 | 57 | 62 (94) |
| Phycomyces Lipase oleocapsules; Example 51 | 53 | 60 (91) |

( ): Index of specific activity
**: Lipase activity per absorbance 1.000 at 280 nm corresponding to a unit amount of the protein.

We claim:

1. A method of producing a microencapsulated product, which comprises
   (a) dissolving an oil-and-fat in an organic solvent by heating at a temperature within the range from 50° C to 100° C, said oil-and-fat being solid at room temperature, and melting at a temperature not lower than 30° C, said organic solvent being hardly or not capable of dissolving a core material to be encapsulated but capable of dissolving not less than 1 percent (weight/volume) of said oil-and-fat when hot and capable of coacervating not less than 50 percent of the dissolved oil-and-fat when cold,
   (b) dispersing said core material in the resultant solution, said dispersion having the oil-and-fat at the ratio of 0.1–10:1 relative to the core material by weight basis and having the organic solvent at the ratio of at least 3:1 relative to the core material by volume/weight basis,
   (c) cooling the dispersion to a temperature lower than 60° C with stirring to coacervate the oil-and-fat on the core material, and
   (d) separating and drying the resultant encapsulated particulate product.

2. The method according to claim 1, wherein the dissolution of the oil-and-fat is carried out at a temperature near the boiling point of the employed solvent.

3. The method according to claim 1, wherein the oil-and-fat is a hydrogenated oil-and-fat, solid fat, or synthetic solid glyceride.

4. The method according to claim 3, wherein the hydrogenated oil-and-fat is hydrogenated castor oil, hydrogenated soybean oil, hydrogenated rapeseed oil, hydrogenated beef tallow, hydrogenated palm oil, hydrogenated cottonseed oil, hydrogenated fish oil or hydrogenated whale oil.

5. The method according to claim 4, wherein the hydrogenated oil-and-fat is one having a melting point not lower than 50° C.

6. The method according to claim 5, wherein the hydrogenated oil-and-fat is hydrogenated castor oil or hydrogenated soybean oil.

7. The method according to claim 1, wherein the organic solvent is lower alkanol, saturated hydrocarbon, ethyl ether, ethylene glycol monomethyl ether, ethyl acetate, acetone, benzene, trichloroethylene or a mixture thereof.

8. The method according to claim 7, wherein the lower alkanol is methanol, ethanol, n-propanol or iso-propanol.

9. The method according to claim 7, wherein the saturated hydrocarbon is n-hexane or cyclohexane.

10. The method according to claim 7, wherein the mixture is lower alkanol and saturated hydrocarbon.

11. The method according to claim 1, wherein the core material is solid at room temperature having diameter within the range of 0.1 micron to 3 millimeters.

12. The method according to claim 11, wherein the core material is one which is employed as feed additive, medicine, agricultural chemical or food additive.

13. The method according to claim 11, wherein the core material is vitamin, mineral, amino acid, antibiotic, synthetic antibacterial or antiprotozoal agent, analgesic antipyretic, enzyme, dried viable microorganism, feed or food material, or agricultural chemical.

14. The method according to claim 13, wherein the antibiotic is one of macrolide antibiotics, tetracyclines, penicillins, cephalosporins, polypeptide antibiotics, aminoglycosidic antibiotics and polyether antibiotics.

15. The method according to claim 1, wherein the core material is thiamine salt or its derivative.

16. The method according to claim 1, wherein the core material is ascorbic acid or it salt.

17. The method according to claim 1, wherein the core material is pyridoxine hydrochloride.

18. The method according to claim 1, wherein the core material is menadione or its derivative.

19. The method according to claim 1, wherein the core material is folic acid.

20. The method according to claim 1, wherein the core material is methionine.

21. The method according to claim 1, wherein the core material is one of macrolide antibiotics.

22. The method according to claim 1, wherein the core material is one of aminoglycosidic antibiotics.

23. The method according to claim 1, wherein the core material is enzyme.

24. The method according to claim 1, wherein the core material is dried viable microorganism.

25. The method according to claim 1, wherein the step (a) is carried out by dissolving a polymer together with an oil-and-fat in an organic solvent to make a concentration of the polymer in the organic solvent not greater than 5 (weight/volume) percent, and to make the ratio of the polymer in the coacervated oil-and-fat of the encapsulated particulate product in the step (d) not greater than 25 percent by weight basis.

26. The method according to claim 25, wherein the polymer is cellulose derivative or acrylic copolymer.

27. The method according to claim 1, wherein the resultant dried particulate product in the step (d) is further mixed with a powdery hydrophobic carrier, heated and then cooled.

28. The method according to claim 27, wherein the heating is carried out at a temperature higher than a melting point of the employed oil-and-fat by degrees not more than ten in centigrade.

29. The method according to claim 28, wherein the heating is carried out at a temperature within the range from 30° to 90° C.

30. The method according to claim 27, wherein the amount of the powdery hydrophobic carrier is 0.1 to 5 times as much as the dried particulate product by weight basis.

31. The method according to claim 27, wherein the cooling is carried out to a temperature lower than a melting point of the employed oil-and-fat.

32. A microencapsulated product which is obtainable by the method of claim 1.

* * * * *